(12) United States Patent
Chemin et al.

(10) Patent No.: US 7,479,386 B2
(45) Date of Patent: Jan. 20, 2009

(54) HXHV VIRUS, NUCLEIC MATERIAL, PEPTIDE MATERIAL AND USES

(75) Inventors: Isabelle Chemin, Caluire (FR); Christian Trepo, Bron (FR); Frederic Bedin, Lyons (FR); Colette Jolivet Reynaud, Saint Bonnet de Mure (FR)

(73) Assignee: Institut National de la Recherche Medicale, Paris (FR)

( * ) Notice: Subject to any disclaimer, the term of this patent is extended or adjusted under 35 U.S.C. 154(b) by 358 days.

(21) Appl. No.: 10/499,805

(22) PCT Filed: Dec. 27, 2002

(86) PCT No.: PCT/FR02/04578

§ 371 (c)(1),
(2), (4) Date: Oct. 12, 2004

(87) PCT Pub. No.: WO03/055994

PCT Pub. Date: Jul. 10, 2003

(65) Prior Publication Data

US 2005/0037336 A1    Feb. 17, 2005

(30) Foreign Application Priority Data

Dec. 28, 2001  (FR) .................................. 01 17048

(51) Int. Cl.
| | |
|---|---|
| C12N 7/00 | (2006.01) |
| C12N 15/33 | (2006.01) |
| C12N 5/10 | (2006.01) |
| C12N 1/19 | (2006.01) |
| C12N 15/09 | (2006.01) |
| C07K 14/18 | (2006.01) |
| A61K 39/12 | (2006.01) |
| A61K 48/00 | (2006.01) |
| C12Q 1/70 | (2006.01) |
| C12Q 1/68 | (2006.01) |
| C07H 21/00 | (2006.01) |

(52) U.S. Cl. ................. 435/235.1; 424/204.1; 424/93.2; 435/5; 435/6; 435/69.3; 435/320.1; 435/362; 435/365; 435/254.21; 435/254.23; 536/23.72; 536/24.32; 536/24.33; 514/44

(58) Field of Classification Search ........................ None
See application file for complete search history.

(56) References Cited

U.S. PATENT DOCUMENTS 6,551,795 B1 *   4/2003   Rubenfield et al. ......... 435/69.1

OTHER PUBLICATIONS

Simmonds P. "Structure constaints on RNA virus evolution" J. Virology vol. 73(1999), N. 7, pp. 5787-5794.*
Haynes BF. HIV vaccines: where we are and where we are going. Lancet. Oct. 5, 1996;348(9032):933-7. Review.*

(Continued)

Primary Examiner—Mary E Mosher
Assistant Examiner—Stuart W Snyder
(74) Attorney, Agent, or Firm—Oliff & Berridge, PLC

(57) ABSTRACT

Isolated HXHV virus having the following characteristics:
  (i) a DNA genome which is at least partially single-stranded,
  (ii) the said genome comprises one reading frame (ORF) encoding one protein or one polyprotein
  (iii) the said genome comprises a nucleotide sequence which exhibits, for any segment of at least 40 nucleotides belonging to the said sequence, at least 90% homology with SEQ ID NO: 1 or with its complementary sequence,
nucleic material and peptide material and uses.

18 Claims, 1 Drawing Sheet

ELISA 1/50

OTHER PUBLICATIONS

John P. Moore & Dennis R. Burton. HIV-1 neutralizing antibodies: How full is the bottle? Nature Medicine (1999) 5, 142-144.*

Dennis R. Burton & John P. Moore. Why do we not have an HIV vaccine and how can we make one? Nat Med. May 1998; 4(5s):495-498.*

Desrosiers RC. Prospects for an AIDS vaccine. Nat Med. Mar. 2004;10(3):221-3.*

Stover, et al. Complete genome sequence of *Pseudomonas aeruginosa* PA01, and opportunmistic pathogen. Nature. 2000; 406:959-964.*

F. Denis et al; "Les nouveaux virus des hépatites, E GB et suivants. New Hepatitis Viruses E, GB and Next"; *Transfusion Clinique et Biologique*; Arnette-Blackwell; Paris, FR; vol. 3, No. 1, 1996, pp. 19-25; XP000612674.

D. Bowden et al.; "New Hepatitis Viruses: Are There Enough Letters in the Alphabet?"; *Medical Journal of Australia*; vol. 164, No. 2, 1996, pp. 87-89; XP000612664.

Achim Kramer et al.; "A General Route to Fingerprint Analyses of Peptide-Antibody Interactions Using a Clustered Amino Acid Peptide Library: Comparison with a Phage Display Library"; *Molecular Immunology*; vol. 32, No. 7, pp. 459-465, 1995.

G. Köhler et al.; "Continuous cultures of fused cells secreting antibody of predefined specificity"; *Nature*; vol. 256, Aug. 7, 1975, pp. 495-497.

G. Galfre et al.; "Antibodies to major histocompatibility antigens produced by hybrid cell lines"; *Nature*; vol. 266, Apr. 7, 1977, pp. 550-552.

A. Roda et al.; "Production of a High-Titer Antibody to Bile Acids", *Journal of Steroid Biochemistry*; vol. 13, 1980, pp. 449-454.

Peter T. Jones et al.; "Replacing the complementarity-determining regions in a human antibody with those from a mouse"; *Nature*; vol. 321, May 29, 1986, pp. 522-525.

Lutz Riechmann et al.; "Reshaping human antibodies for therapy"; *Nature*; vol. 332; Mar. 24, 1988, pp. 323-327.

Leonard G. Presta; "Antibody engineering"; *Current Opinion in Structural Biology*; 1992, 2: pp. 593-596.

Bruce R. Blazar et al.; "Anti-CD3eF(ab')$_2$ Fragments Inhibit T Cell Expansion in Vivo During Graft-Versus-Host Disease or the Primary Immune Response to Nominal Antigen[1,2]"; *The Journal of Immunology*; 1997, 159: pp. 5821-5833.

Robert E. Bird et al.; "Single-Chain Antigen-Binding Proteins"; *Science*; vol. 242, Oct. 21, 1988, pp. 423-426.

Fumiko Arakawa et al.; "Cloning and Sequencing of the $V_H$ and $V_K$ genes of an Anti-CD3 Monoclonal Antibody, and Construction of a Mouse/Human Chimeric Antibody[1]"; *Journal of Biochemistry*; vol. 120, No. 3, 1996, pp. 657-662.

Vijay K. Chaudhary et al.; "A recombinant immunotoxin consisting of two antibody variable domains fused to *Pseudomonas* exotoxin"; *Nature*; vol. 339, Jun. 1, 1989, pp. 394-397.

R. Bruce Wallace et al.; "Hybridization of synthetic oligodeoxyribonucleotides to Φx174 DNA: the effect of single base pair mismatch"; *Nucleic Acids Research*; vol. 6, No. 11, 1979, pp. 3543-3557.

R. Bruce Wallace et al.; "Direction Deletion of a Yeast Transfer RNA Intervening Sequence"; *Science*; vol. 209, Sep. 19, 1980, pp. 1396-1400.

Keiichi Itakura et al.; "Chemical DNA Synthesis and Recombinant DNA Studies"; *Science*; vol. 209, Sep. 19, 1980, pp. 1401-1405.

Sidney V. Suggs et al.; "Use of synthetic oligonucleotides as hybridization probes: Isolation of cloned cDNA sequences for human β2-microglobulin"; *Biochemistry*; vol. 78 No. 11, Nov. 1981, pp. 6613-6617.

R. Bruce Wallace et al.; "The use of synthetic oligonucleotides as hybridization probes. II. Hybridization of oligonucleotides of mixed sequence to rabbit β-globin DNA"; *Nucleic Acids Research*; vol. 9, No. 4, 1981, pp. 879-894.

R. Bruce Wallace et al.; "Oligonucleotide directed mutagenesis of the human β-globin gene: a general method for producing specific point mutations in cloned DNA"; *Nucleic Acids Research*; vol. 9, No. 15, 1981, pp. 3647-3656.

Brenda J. Conner et al.; "Detection of sickle cell $β^s$-globin allele by hybridization with synthetic oligonucleotides"; *Medical Sciences*; vol. 80, Jan. 1983, pp. 278-282.

Philippe Cros et al.; "Monoclonal antibodies targeted to α-oligonucleotides. Characterisation and application in nucleic acid detection"; *Nucleic Acids Research*; vol. 22, No. 15, 1994, pp. 2951-2957.

Wayne F. Anderson et al.; "Antibodies to DNA"; *BioEssays*; vol. 8, No. 2, Feb./Mar. 1988, pp. 69-74.

Jeremy S. Lee et al.; "Functional groups on 'Z' DNA recognized by monoclonal antibodies"; *Febs Letters*; vol. 168, No. 2, Mar. 1984, pp. 303-306.

Bernard Malfoy et al.; "Interaction between Antibodies to Z-Form Deoxyribonucleic Acid and Double-Stranded Polynucleotides"; Biochemistry; vol. 21, No. 22, 1982, pp. 5463-5467.

David Stollar; "The Experimental Induction of Antibodies to Nucleic Acids"; Methods in Enzymology; vol. 70, 1980, pp. 70-85.

F. Traincard et al.; "Monoclonal anti-nucleoside antibodies—Characterization and application in an enzyme immunoassay of single-stranded DNA"; *Journal of Immunological Methods*; vol. 123, 1989, pp. 83-91.

Francois Traincard et al.; "Calibration of target amounts of DNA in hybridization experiments using monoclonal anti-nucleoside antibodies"; *Molecular and Cellular Probes*; 1989, pp. 27-38.

Isabelle Chemin et al.; "High incidence of hepatitis B infections among chronic hepatitis cases of unknown aetiology"; *Journal of Hepatology*; vol. 34, 2001, pp. 447-454.

Giovanni Raimondo; "Occult hepatitis B virus infection and liver disease: fact or fiction?" *Journal of Hepatology*; vol. 34, 2001, pp. 471-473.

Minoru Shibata et al.; "The Presence of Newly Identified Infectious Agent (SEN Virus) in Patients with Liver Disease and in Blood Donors in Japan"; *The Journal of Infectious Diseases*; vol. 184, 2001, pp. 400-404.

* cited by examiner

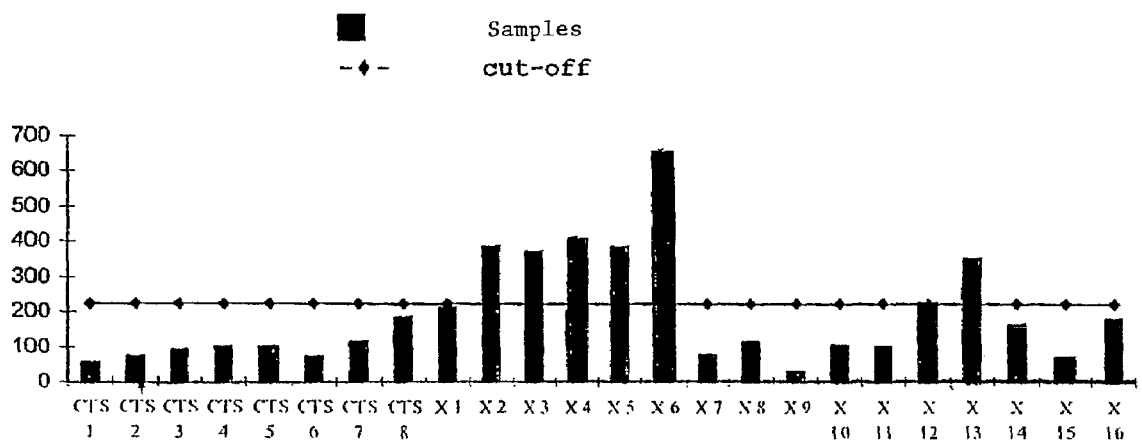
FIGURE
ELISA 1/50

HXHV VIRUS, NUCLEIC MATERIAL, PEPTIDE MATERIAL AND USES

Hepatitis is the most important of the transmissible diseases. The mode of transmission is most often transfusion, organ transplants and haemodialysis, but hepatitis can also be transmitted by ingestion of contaminated food or water and by contact between individuals.

Viral hepatitis are induced by various viral agents which are distinguishable from each other by their genomes and their modes of replication. Viral hepatitis cause damage to the liver with varying degrees of severity. More than a billion people worldwide suffer from viral hepatitis. Serious risks exist in the chronic forms of hepatitis which can progress to cirrhosis or hepatocarcinoma. Viral hepatitis can be diagnosed by the detection of well-defined symptoms, such as jaundice, high levels of transaminases (aspartate transaminase or AST, alanine transaminase or ALT, lactate dehydrogenase or LDH), and hepatic lesions. Despite the knowledge of various hepatitis A, B, C, D, E, G and TTV viruses, 5% of all hepatitis and 40% of fulminant hepatitis remain unexplained, hence the hypothesis of the existence of unknown hepatitis viruses. These hepatitis of unknown aetiology are both post-transfusional and sporadic, chronic or fulminant. They are commonly called hepatitis X.

Hepatitis G (GBV-A, GBV-B, GBV-C) and TTV viruses recently identified do not appear to be pathogenic in humans and cannot therefore explain the cases of hepatitis of unknown aetiology or hepatitis X.

From one case of serious hepatitis of unknown aetiology, in a patient in whom a treatment with interferon made it possible to normalize transaminases, the present inventors were able to clone, by means of the "RDA" (Representational Difference Analysis) subtractive hybridization technique, the nucleic acids differentially expressed between the serum at the transaminase peak and the serum after normalization of the transaminases. 643 clones representing DNA sequences specific to serum at the transaminase peak were screened. In order to exclude the possibility of homologies with the human genome or any other known sequence, various routes were explored:

hybridization of the 643 clones with a "human genomic DNA" sonde, which made it possible to show that 593 clones hybridize with the "human genomic DNA" probe and that 50 clones do not hybridize with the "human genomic DNA" probe and comprise an insert, search in the data banks for possible homologies between the sequences of these 50 clones and the published sequences, using the BLAST program at the NCBI site according to the parameters given by the site, additional screening of 4 clones selected from the preceding step by "Dot blot" on the DNA of the clones selected using a radioactively labelled "human genomic DNA" probe and by Southern blotting of human genomic DNA using, as probe, the radioactively labelled clones selected.

At the end of these various steps, 2 DNA clones were selected of which the sequences were unknown in data banks. By virtue of PCRs performed within the cloned sequences, tested on human genomic DNA obtained from blood donors, in the end a single clone containing an insert of 1400 base pairs was selected for its lack of homology with the human genomic DNA and with any sequences present in the data banks. The sequence of this clone was called XH. This sequence is rich in GC (62%) and has four open reading frames. This isolated sequence was then characterized by four parallel studies:

bioclinical and epidemiological study,
molecular study,
production of specific antibodies,
electron microscopy study.

The results show that:

the XH sequence is found by PCR by means of specific primers in 10% of patients carrying a chronic hepatitis of unknown aetiology present in the study (out of 110 patients tested), this sequence is absent from the blood donors tested by the same PCR specific for the cloned XH sequence, this sequence is a DNA sequence which is at least partially single-stranded, it has several reading frames and one of the reading frames encodes a protein of 21 kD, which protein possesses a region which exhibits all the immunogenicity and hydrophilicity properties required to induce the production of antibodies, fractionation on sucrose gradients of a serum of a patient non-A-E positive by PCR for the XH sequence (XH+) made it possible to isolate two consecutives fractions (1.3-1.5 g/cm$^3$) positive for the XH sequence in which were detected particles whose size and regularity are compatible with those of a viral agent. These particles are not observed in the gradient fractions negative by PCR for the XH sequence. This novel infectious agent was called HXHV.

BRIEF DESCRIPTION OF THE DRAWING

The FIGURE is a graph of results of ELISA test using SEQ ID NO:6 for the capture of antibodies specific for the HXHV virus potentially present in patients having chronic non-A, non-E hepatitis.

DETAILED DESCRIPTION OF EMBODIMENTS

Accordingly, the present invention relates to the isolated HXHV virus and provides nucleic acids and polypeptides which are capable of being derived from HXHV. Furthermore, the invention provides the means for diagnosing an HXHV virus infection in patients or animals suspected of having a viral hepatitis and the pharmaceutical or vaccine compositions for preventing or treating the disease associated with the infection.

Thus, the present invention relates to the isolated HXHV virus exhibiting the following characteristics:

(i) a DNA genome which is at least partially single-stranded, (ii) the said genome comprises one or more reading frames (ORF) encoding one or more proteins or polyproteins;

(iii) the said genome comprises a nucleotide sequence capable of hybridizing with the sequence SEQ ID NO: 1 or with the sequence complementary to SEQ ID NO: 1; preferably, it has a nucleotide sequence which exhibits, for any segment of at least 40 nucleotides belonging to the said sequence, at least 90%, advantageously at least 95%, or better still at least 98%, homology with SEQ ID NO: 1 or with its complementary sequence;

a nucleic acid sequence capable of being obtained from the genome of the HXHV virus or fragments of the said genome or a nucleic acid sequence homologous to the said nucleic acid sequence SEQ ID NO: 1 or to the sequence complementary to SEQ ID NO: 1, and exhibiting at least 90%, preferably at least 95%, and advantageously at least 98%, homology over the length of the sequence represented in SEQ ID NO: 1; the virus having the characteristics defined above;

a DNA or RNA nucleotide fragment comprising or consisting of a DNA or RNA nucleotide sequence of at least 12 contiguous nucleotides, preferably of at least 15 or 18 contiguous nucleotides, and advantageously of at least 21 contiguous nucleotides, of the DNA nucleotide sequence SEQ ID NO: 1 or of a nucleotide sequence which exhibits at least 90%, for example at least 95% or 98% homology with respect to the sequence represented in SEQ ID NO: 1 or of their complementary DNA sequences or of the product of transcription of the said DNA nucleotide sequences; in particular, a fragment in which the said contiguous nucleotides belong to one of the following segments: a segment whose sequence starts at nucleotide 813 and ends at nucleotide 1361 of SEQ ID NO: 1 and a segment whose sequence starts at nucleotide 927 and ends at nucleotide 968 of SEQ ID NO: 1, the complementary fragment and the product of transcription of the said fragments and a fragment comprising or consisting of SEQ ID NO: 1 or its complementary DNA sequence or a sequence which is the product of transcription of SEQ ID NO:1;

a DNA molecule which comprises or consists of a DNA nucleotide sequence represented in SEQ ID NO: 1 or in that it comprises at least one DNA nucleotide fragment as defined above or their complementary sequences;

an RNA molecule which comprises or consists of an RNA nucleotide sequence which is the product of transcription of a DNA nucleotide sequence represented in SEQ ID NO: 1 or of at least one of its fragments as defined above or their complementary sequences.

The above homology covers the functional equivalents of the sequence SEQ ID NO: 1, that is to say the DNA sequences in which at least one codon can be replaced by another codon while encoding an identical amino acid. This is referred to as degeneracy of the genetic code. Thus, the codes for arginine, for serine and for leucine exhibit a degeneracy of the order 6 (that is to say that there are six different codons for each of them), whereas the codes for the other amino acids, such as glutamic acid, glutamine, tyrosine, histidine and a few others exhibit a degeneracy of the order 2. Of all the amino acids, only tryptophan and methionine have a degeneracy of the order 1. It is therefore clear that for the expression of a polypeptide whose sequence is for example represented in SEQ ID NO: 6, it is possible to use variants and functional nucleic acid sequences in which the codon compositions are different from the nucleic acid sequence represented in SEQ ID NO: 1.

The homology defined above also relates to the mutants of the HXHV virus, and in particular those derived from natural variability. Indeed, it is well known to specialists that the viruses have relatively high levels of spontaneous or induced mutations.

The invention also relates to a polypeptide comprising a polypeptide sequence or at least one of its fragments, characterized in that the said polypeptide sequence is encoded by the genome of the HXHV virus or by fragments of the said genome, or by their functional equivalents or by a nucleotide sequence which exhibits at least 90% homology, preferably at least 95% homology and advantageously at least 98% homology with respect to the sequence represented in SEQ ID NO: 1 and in that the virus has the characteristics determined above;

a polypeptide fragment, characterized in that it comprises or consists of a peptide sequence of at least 4 amino acids, preferably of at least 5 or 6 amino acids and advantageously of at least 7 amino acids, preferably still of at most 15 amino acids, in particular from 6 to 15 amino acids and advantageously from 6 to 10 or from 8 to 12 amino acids of the peptide sequence represented in SEQ ID NO: 5 or of a peptide sequence functionally equivalent to SEQ ID NO: 5. The inventors have in particular shown that in the sequence SEQ ID NO: 5, there is a region of 14 amino acids which exhibits all the required immunogenicity and hydrophilicity properties required to induce a humoral response. This polypeptide of 14 amino acids is identified in SEQ ID NO: 6. They have also shown that this polypeptide of 14 amino acids corresponds to an antigenic region of the sequence represented in SEQ ID NO: 5 since it has made it possible to develop an ELISA test protocol for the detection of anti-HXHV antibodies in patients having chronic non-A non-E hepatitis; an advantageous polypeptide fragment comprises or consists of SEQ ID NO: 6 or a polypeptide sequence functionally equivalent to SEQ ID NO: 6;

a polypeptide fragment which comprises or which consists of a peptide sequence represented in SEQ ID NO: 5 or a peptide sequence functionally equivalent to SEQ ID NO: 5.

"Polypeptide" denotes a peptide, in the isolated state, having a succession of a variable number of amino acids, such as an oligopeptide, a protein, a fusion protein, a fusion peptide, a synthetic peptide. A polypeptide may be obtained by various techniques well known to a person skilled in the art, and in particular by chemical synthesis or by genetic recombination techniques. The polypeptides according to the invention may be obtained by conventional methods of synthesis, for example with an automated peptide synthesizer, or by genetic engineering techniques comprising the insertion of a DNA sequence encoding the said polypeptide into an expression vector such as a plasmid or a virus, and the transformation of cells with this expression vector and culturing of these cells.

The expression peptide sequence equivalent to a reference peptide sequence is understood to mean an amino acid sequence modified by insertion and/or deletion and/or substitution and/or extension and/or shortening and/or chemical modification of one or more amino acids, as long as these modifications substantially preserve or even develop the immunoreactive properties of the said reference peptide sequence.

Thus, the expression functionally equivalent sequences which preserve the immunoreactive properties of SEQ ID NO: 5 is understood to mean in particular the sequences in which one or more amino acids are substituted by one or more other amino acids; the sequences in which one or more amino acids of the L series are replaced by an amino acid of the D series, and vice versa; the sequences into which a modification of the amino acid side chains is introduced, such as an acetylation of the amine functional groups, a carboxylation of the thiol functional groups, an esterification of the carboxylic functional groups; a modification of the peptide bonds such as for example of the carba, retro, inverso, retro-inverso, reduced and methyleneoxy bonds.

For example, one or more amino acids in the sequences of the polypeptides of the invention may be substituted by one or more other amino acids of similar polarity which act as functional equivalents. Substitutions for an amino acid in polypeptide sequences of interest may be determined from other members of the class to which the amino acid belongs. For example, the nonpolar (hydrophobic) amino acids comprise alanine, leucine, isoleucine, valine, proline, phenylalanine, tryptophan and methionine. The polar neutral amino acids comprise glycine, serine, threonine, cysteine, tyrosine, asparagine and glutamine. The positively charged (basic)

amino acids comprise arginine, lysine and histidine. The negatively charged (acidic) amino acids comprise aspartic acid and glutamic acid. Other substitutions for an amino acid in polypeptide sequences of interest may be determined from the information contained in the article by Kramer A. et al. (*Molecular Immunology*, Vol. 32, No. 7, pp. 459-465 (1995)). These authors have set up banks in which, in order to reduce the problem of combinatory explosion of the number of molecules, they used groups of amino acids consisting of amino acids having similar physicochemical properties and it is the amino acids grouped together in each of these six groups, listed below, which are considered mainly as equivalents in the present invention.

Group 1: alanine, proline, glycine.
Group 2: aspartic acid, glutamic acid.
Group 3: histidine, lysine, arginine.
Group 4: asparagine, glutamine, serine, threonine.
Group 5: phenylalanine, tyrosine, tryptophan.
Group 6: isoleucine, leucine, valine, methionine.

The equivalence for a peptide sequence with respect to a reference peptide sequence may be defined by its identity or its homology, expressed as a percentage, with the said reference sequence. This percentage is determined, for a sequence of a given number of contiguous amino acids, by alignment of the two sequences, moving one with respect to the other, and comparing the amino acids in the two sequences. The percentage of identity is determined from the number of amino acids which are identical to the amino acids of the reference sequence, in the same position. The percentage homology is determined from the number of amino acids which are equivalent to amino acids of the reference sequence, in the same position.

The invention also relates to an expression cassette which is functional in a cell derived from a prokaryotic or eukaryotic organism allowing the expression of a nucleic acid sequence or of a DNA fragment or of a DNA molecule as described above, placed under the control of elements necessary for its expression. The expression cassette is characterized in that it is functional in a cell derived from a prokaryotic organism, in particular *E. coli*, or from a eukaryotic or lower eukaryotic organism, in particular COS and CHO cells and *Saccharomyces cerevisiae* and *Pichia pastoris* cells.

The invention also relates to a vector comprising the said expression cassette; a cell derived from a prokaryotic organism, such as *E. coli* or a eukaryotic organism, preferably a eukaryotic or lower eukaryotic organism, and advantageously a COS or CHO cell or a cell derived from *Saccharomyces cerevisiae* or *Pichia pastoris* comprising an expression cassette or a vector as defined above; and the polypeptide produced by the expression cassette, the vector or the cell.

The subject of the invention is a method for preparing a polypeptide or a polypeptide fragment as defined above which consists in cultivating a host cell satisfying the preceding definitions, in an appropriate culture medium, the said host cell being transformed with an expression vector which contains a DNA nucleic acid sequence as defined above or a DNA nucleic fragment as defined above or a DNA molecule as defined above, and in purifying the said polypeptide produced to a required degree of purity.

The subject of the invention is also an immunogenic polypeptide, characterized in that it has a peptide sequence or in that it consists of a polypeptide as defined above, in particular the polypeptide represented in SEQ ID NO: 6. Such an immunogenic polypeptide is used for the production of monoclonal or polyclonal antibodies or of fragments of the said antibodies and the invention encompasses the monoclonal or polyclonal antibodies or fragments thereof, being obtained by immunizing a mammalian animal (rabbit, rat, mouse) with such an immunogenic peptide.

The production of monoclonal or polyclonal antibodies is well known to a person skilled in the art. There may be mentioned by way of reference Köhler G. and Milstein C. (1975): Continuous culture of fused cells secreting antibody of predefined specificity, Nature 256:495-497 and Galfre G. et al. (1977) Nature, 266: 522-550 for the production of monoclonal antibodies and Roda A., Bolelli G. F.: Production of high-titer antibody to bile acids, Journal of Steroid Biochemistry, Vol. 13, pp 449-454 (1980) for the production of polyclonal antibodies. Antibodies may also be produced by immunizing mice, rats or rabbits with the HXHV viral particles. For the production of polyclonal and monoclonal antibodies, the immunogen may be coupled to serum albumin (peptide SA) or to Keyhole Lympet haemocyanin (peptide KLH) as support for the immunization. In the context of the present invention, the immunogen identified in SEQ ID NO: 6 is coupled to BSA (bovine serum albumin). The animals are subjected to several injections of immunogen, the antibodies are collected from the serum, purified (brought into contact with a "normal" liver powder) and are then screened for their specificity using the usual techniques, such as ELISA or Western blot tests. For the production of monoclonal antibodies, the animals are subjected to an injection of immunogen using Freund's complete adjuvant. The sera and the hybridoma culture supernatants obtained from the immunized animals are analysed for their specificity and their selectivity using conventional techniques, such as for example ELISA or Western blot tests. The hybridomas producing the most specific and the most sensitive antibodies are selected. Monoclonal antibodies may also be produced in vitro by cell culture of the hybridomas produced or by recovering ascitic fluid, after intraperitoneal injection of the hybridomas into mice. Regardless of the mode of production, as a supernatant or as an ascitic fluid, the antibodies are then purified. The methods of purification used are mainly filtration on an ion-exchange gel and exclusion chromatography or affinity chromatography (protein A or G). A sufficient number of antibodies are screened in functional tests for identifying the most efficient antibodies. The in vitro production of antibodies, of antibody fragments or of antibody derivatives, such as chimeric antibodies produced by genetic engineering, is well known to persons skilled in the art. It is advantageous to use humanized antibodies. The "humanized" forms of nonhuman antibodies, for example murine antibodies, are chimeric antibodies which comprise a minimal sequence derived from a nonhuman immunoglobulin. For the majority, the humanized antibodies are human immunoglobulins (receptor antibody) in which the residues of a hypervariable region of the receptor are replaced by residues of a hypervariable region of a nonhuman donor species (donor antibody), such as mice, rats, rabbits or nonhuman primates, having the desired specificity, affinity and capacity. In some cases, the residues (FR) of the Fv region of the human immunoglobulin are replaced by corresponding nonhuman residues. Furthermore, the humanized antibodies may comprise residues which are not found in the recipient antibody or in the donor antibody. These modifications are performed in order to improve the performance of the antibody. In general, the humanized antibody will comprise at least, and preferably, two variable domains, in which all or nearly all the hypervariable loops correspond to a nonhuman immunoglobulin and all or nearly all the FR regions will be those of a human immunoglobulin. The humanized antibodies may optionally also comprise at least part of a constant (Fc) region of an immunoglobulin, such as a human immunoglobulin (Jones et al., Nature 321: 522-525

(1986); Reichmann et al., Nature 332: 323-329 (1988); and Presta et al., Curr. Op. Struct. Biol. 2: 593-596 (1992).

More particularly, the expression antibody fragment is understood to mean the F(ab)2, Fab, Fab', sFv fragments (Blazar et al., 1997, Journal of Immunology 159: 5821-5833 and Bird et al., 1988, Science 242: 423-426) of a native antobidy and the expression derived is understood to mean, inter alia, a chimeric derivative of a native antibody (see for example Arakawa et al., 1996, J. Biochem 120: 657-662 and Chaudray et al., 1989, Nature 339: 394-397). These antibody fragments and antibody derivatives preserve the capacity to selectively bind to the target antigen.

The monoclonal or polyclonal antibody thus obtained or its fragment is incorporated into a diagnostic composition which is used in a method for detecting at least one polypeptide or one polypeptide fragment as defined above in a biological sample, according to which the biological sample is brought into contact with the composition under predetermined conditions which allow the formation of antibody/antigen complexes and the formation of the said complexes is detected.

The subject of the invention is also a diagnostic composition which comprises a polypeptide or a polypeptide fragment as defined above and a method for detecting antibodies directed against the HXHV virus or at least against a polypeptide or a polypeptide fragment of the invention, according to which a biological sample suspected of being or of having possibly been infected with the HXHV virus is brought into contact with the diagnositic composition under predetermined conditions which allow the formation of antibody/antigen complexes and the formation of the said complexes is detected. The method described in the experimental part of the appended figure clearly shows that the polypeptide of the invention or the polypeptide fragment SEQ ID NO: 6 makes it possible to detect antibodies specific for the HXHV virus in patients having a non-A, non-E hepatitis.

It is known that during an infection by a viral agent, the host develops antibodies directed against this viral agent (humoral response). It is shown in the experimental part that the immunization of rabbits with an immunogen of the invention allows the producction of antibodies by the rabbits. It has also been shown that patients having a non-A, non-E hepatitis developed antibodies directed against the HXHV virus. The subject of the present invnetion is therefore also the biological material for the preparation of a pharmaceutical composition intended for the treatment of human beings or of animals infected with at least the HXHV virus and immunogenic preparations which may be used to produce therapeutic vaccines against an HXHV virus infection and prophylactic vaccines for preventing a potential HXHV virus infection, the said immunogenic preparations comprising:

(i) either at least one natural, recombinant or synthetic polypeptide or polypeptide fragment of the invention; or (ii) the HXHV virus, for example in an attenuated or mutated form.

The subject of the present invention is also the use of at least one monoclonal or polyclonal antibody or of at least one fragment of the said antibodies of the invention, specific for at least one polypeptide or a polypeptide fragment as defined above in (i) for the preparation of a pharmaceutical composition which, when administered to a patient infected with the HXHV virus, has the capacity to reduce or even inhibit the proliferation and/or replication of the virus. These antibodies or fragments thereof are called neutralizing antibodies.

Consequently, the invention relates to an immunogenic or vaccine composition, characterized in that it comprises a polypeptide or a polypeptide fragment of the invention or the HXHV virus, optionally combined with an appropriate vehicle and/or adjuvant and/or diluent and/or with a pharmaceutically acceptable excipient; and to a pharmaceutical composition comprising a biological material as defined above, optionally combined with an appropriate vehicle and/or adjuvant and/or diluent and/or with a pharmaceutically acceptable excipient.

The expression biological sample is understood to mean for example blood, serum, plasma, tissue samples, such as liver biopsy extracts.

The vaccines prepared are injectable, that is to say in liquid solution or in suspension. Optionally, the preparation may also be emulsified. The antigenic molecule may be mixed with excipients which are pharmaceutically acceptable and compatible with the active ingredient. Examples of favourable excipients are water, a saline solution, dextrose, glycerol, ethanol or equivalents and combinations thereof. If desired, the vaccine may contain minor quantities of auxiliary substances such as wetting or emulsifying agents, pH-buffering agents or adjuvants such as aluminium hydroxide, the muramyl dipeptide or variations thereof. In the case of peptides, their coupling to a larger molecule (KLH, tetanus toxin) sometimes increases immunogenicity. The vaccines are conventionally administered by injection, for example intramuscularly. Additional favourable formulations with other modes of administration include suppositories and sometimes oral formulations.

The expression "pharmaceutically acceptable vehicle" is understood to mean carriers and vehicles administrable to human beings or to an animal, as described for example in Remington's Pharmaceutical Sciences $16^{th}$ ed., Mack Publishing Co. The pharmaceutically acceptable vehicle is preferably isotonic, hypotonic or has low hypertonicity and a relatively low ionic strength. The definitions of pharmaceutically acceptable excipients and adjuvants are also given in Remington's Pharmaceutical Sciences cited above.

The subject of the invention is also a probe, characterized in that it is capable of hybridizing, under defined stringency conditions, with a nucleic acid sequence or with a DNA or RNA nucleotide fragment or with a DNA or RNA molecule of the invention; preferably, a probe of the invention comprises at least 12 nucleotides, and the hybridization is carried out under stringency conditions corresponding to a combination of the temperature and the salt concentration chosen approximately between 12 and 20° C. under the Tm ("melting temperature") of the probe/nucleotide sequence complex to be detected;

a primer, characterized in that it is capable of hybridizing, under defined stringency conditions with a nucleic acid sequence or with a DNA or RNA nucleotide fragment or with a DNA or RNA molecule of the invention preferably, a primer of the invention comprises at least 12 nucleotides, and the hybridization is carried out under stringency conditions corresponding to a combination of the temperature and the salt concentration chosen approximately between 12 and 20° C. under the Tm ("melting temperature") of the primer/nucleotide sequence complex to be amplified and/or detected;

a primer capable of hybridizing with a nucleic sequence or with a nucleotide fragment or with a DNA molecule of the invention, characterized in that it is chosen from any of the sequences SEQ IDs NO: 19 to 22;

an anti-nucleic acid antibody, characterized in that it is capable of binding to a nucleic acid sequence or to a DNA or RNA nucleotide fragment or to a DNA or RNA molecule;

a diagnostic composition, characterized in that it comprises at least one probe or one primer or one anti-nucleic acid antibody as defined above;

a method for detecting viral DNA and/or RNA, according to which a sample is collected from a patient, the said sample is treated if necessary in order to extract the DNA and/or the RNA therefrom, the said sample is brought into contact with at least one probe or one primer of the invention, under defined stringency conditions and the presence of viral DNA and/or RNA in the sample is detected either by demonstrating a hybridization of the said viral DNA and/or RNA with at least one probe, or by amplification of the said DNA and/or RNA; and a method for detecting viral DNA and/or RNA, according to which a serum or plasma sample is collected from a patient, the said sample is treated if necessary in order to extract the DNA and/or RNA therefrom, the said sample is brought into contact with at least one anti-nucleic acid antibody, the said antibody being optionally labelled with any appropriate marker and the formation of a nucleic acid/antibody complex is demonstrated.

The production of polynucleotides, probes or primers forms part of the general knowledge of persons skilled in the art. There may be mentioned in particular the use of restriction enzymes, and chemical synthesis on an automated synthesizer. The probes and primers capable of hybridizing, under determined stringency conditions, with a DNA or RNA nucleotide sequence or with a nucleotide fragment as defined above form part of this definition. It is within the capability of persons skilled in the art to define the appropriate stringency conditions. Characteristic stringency conditions are those which correspond to a combination of the temperature and of the salt concentration chosen approximately between 12 and 20° C. under the Tm ("melting temperature") of the hybrid to be studied. Reference may thus be made to the book by George H. Keller et Mark M. Manak, DNA PROBES, second edition, Stockton Press, 1993, 49 West $24^{th}$ St., New York, N.Y. 10010 USA. The stringency conditions for differentiation of even a single point mutation have been known since at least the period 1979; there may be mentioned by way of examples Wallace R. B et al., DNA. Nucleic. Acids. Res. 6, 3543-3557 (1979), Wallace R. B et al., Science, 209, 1396-1400 (1980), Itakura K. and Riggs A. D., Science, 209, 1401-1405 (1980), Suggs S. V. et al., PNAS, 78, 6613-6617 (1981), Wallace R. B et al. DNA. Nucleic. Acids. Res., 9, 3647-3656 (1981), Wallace R. B et al. DNA. Nucleic. Acids. Res., 9, 879-894 (1981) et Conner B. J. et al, PNAS, 80, 278-282 (1983). Moreover, techniques are known for the production of anti-nucleic acid antibodies. There may be mentioned, by way of examples, Philippe Cros et al., Nucleic Acides Researc, 1994, Vol. 22, No. 15, 2951-2957; Anderson, W. F. et al. (1988) Bioessays, 8 (2), 69-74; Lee, J. S. et al. (1984) FEBS Lett., 168, 303-306; Malfoy, B. et al. (1982) Biochemistry, 21(22), 5463-5467; Stollar, B. D. et al., J. J. (eds) Methods in Enzymology, Academic Press, pp 70-85; Traincard, F. et al. (1989) J. Immunol. Meth., 123, 83-91 and Traincard, F. et al. (1989) Mol. Cell. Probes, 3, 27-38).

The invention also relates to:

a vaccine composition comprising a DNA sequence encoding at least one polypeptide or one polypeptide fragment of the invention, the said DNA being mixed with an appropriate vehicle and/or diluent;

an anti-sense or anti-gene oligonucleotide, characterized in that it is capable of specifically interfering with the synthesis of at least one polypeptide or one polypeptide fragment of the invention;

a pharmaceutical composition, characterized in that it comprises at least one anti-sense oligonucleotide or one anti-gene oligonucleotide;

a vector, characterized in that it comprises at least one gene of therapeutic or vaccine interest, the said gene encoding in particular (i) either at least one polypeptide or one polypeptide fragment of the invention;

(ii) or at least all or part of a polyclonal or monoclonal antibody capable of binding to at least one polypeptide or polypeptide fragment defined in (i);

(iii) or at least one molecule inhibiting at least one polypeptide or polypeptide fragment defined in (i);

(iv) or at least one ligand or any part of a ligand capable of binding to at least one polypeptide or polypeptide fragment defined in (i) and/or of inhibiting its function;

a therapeutic or vaccine composition, characterized in that it comprises, inter alia, a vector as defined in Claim 10 and in that the said gene of interest is placed under the control of elements ensuring its expression in vivo;

a biological material for the preparation of a pharmaceutical or vaccine composition, comprising at least one cell, in particular a cell not naturally producing antibodies, in a form allowing its administration to a human or animal mammalian organism, and optionally its prior culture, the said cell being genetically modified in vitro by at least one nucleic acid sequence containing at least one gene encoding in vivo at least one polypeptide or one polypeptide fragment of the invention or encoding at least one molecule inhibiting the function and/or the binding and/or the expression of at least one polypeptide or of one polypeptide fragment of the invention or encoding at least one antibody or one antibody fragment capable of binding to at least one polypeptide or a polypeptide fragment of the invention;

a genetically modified cell, in particular chosen from eukaryotic cells, such as COS and CHO cells and lower eukaryotic cells, such as yeast cells, in particular cells derived from *Saccaromyces cerevisiae* and *Pichia pastoris*, transformed with at least one nucleic acid sequence or a nucleotide fragment or a DNA molecule or by a vector of the invention; and a pharmaceutical or vaccine composition comprising such a cell.

The pharmaceutical compositions defined above are DNA vaccine compositions which are particularly advantageous, in particular compared with "conventional" vaccine compositions based on a recombinant protein. Indeed, the use for vaccine purposes of recombinant proteins is a cumbersome and expensive system, in particular because it requires very important steps of purification of recombinant antigens. Furthermore, one of the difficulties encountered is of obtaining a sufficiently long persistence of the vaccine to maintain good immune memory. By contrast, the DNA vaccination method, whose advantages are inherent in the intrinsic properties of the DNA, is simple and not very expensive and is simply carried out by intramuscular or intradermal injection. Furthermore, it should be noted that:

DNA vaccines are noninfectious/nonreplicative, because the immunization with DNA is a form of in vivo transfection, the viral antigen is expressed in the mammalian cells in its native conformation, as in the case of a viral infection, a high immune response, both humoral and cellular, is induced, and furthermore, DNA vaccines can be easily combined because of their physicochemical homogeneity.

BRIEF DESCRIPTION OF THE DRAWINGS

The figure labeled "FIGURE, ELISA 1/50" show the results of an ELISA assay to detect anti-HXHV antibodies in 8 control samples and 16 patient samples.

I. MATERIALS AND METHODS

I-1. Source of Biological Material

The material used for the RDA consists of sera archived in a serum bank. The RDA was applied to a case of serious hepatitis of unknown aetiology, successfully treated with IFN. The normalization of the transaminases in this patient after antiviral treatment and especially the relapse after stopping the treatment, with another response during reintroduction of the treatment are elements which militate in favour of a viral aetiology of the disease. A serum sample before treatment and a serum sample after treatment were used for the RDA, the sample before treatment potentially containing the HXHV virus and the sample after treatment few or no viruses.

I-1.1 Preliminary Search for Known Hepatitis Viruses

Screening by Ultrasensitive PCRs:

In order to eliminate the presence of known hepatitis viruses, which could be present in very low quantities or in the form of mutants, very sensitive PCR tests for the hepatitis viruses responsible for chronic hepatitis (B, C, G and TTV) were developed (Chemin et al, J of Hepatol., 2001) which were highly sensitive (detection of 10 viral genomes).

The successive sera from the patient treated with interferon and intended for the subtractive hybridization method remained negative by these tests for all known hepatitis viruses and for the SEN virus (Minoru Shibata et al. The Journal of Infectious Diseases 2001; 184:400-404).

I-1.2 Choice of the Samples for the RDA Procedure

Tester samples or positive controls at the transaminase peak: total nucleic acids extracted from the serum collected at the transaminase peak.

Driver samples or negative controls after treatment: total nucleic acids extracted from the serum collected at the lowest transaminase level.

The extractions of the nucleic acids are carried out with the QIAGEN QIAamp® Viral RNA Mini Kit. The differential technique is carried out using the CLONTECH PCR—Select™ cDNA Subtraction Kit from CLONTECH according to the manufacturer's instructions.

I-2. RDA Procedure

I-2.1 Principle

The method developed by Lysitsyn et al. in 1993 is based on the following principle and the Clontech kit (Clontech PCR-select™ cDNA substraction kit) was used:

Reduction of the Complexity of the Genomic DNA.

The 1st step of the RDA consists in reducing the complexity of the genome. For that, it is necessary to use a restriction enzyme which has a fairly frequent cleavage site, making it possible to reduce the complexity of the genome. The result of this step is the production of a set of sequences of lesser complexity although representative of the initial sequences, hence the term "representational". The preliminary reduction of the complexity of the genome to be studied improves the efficiency of the enrichment steps by facilitating the complete hybridization of the samples.

Enrichment

Adaptors are joined (by means of a ligase) to each end of the DNA fragments of the tester sample containing the viral genome. The driver sample has no adaptors.

During the subtractive hybridization, the tester is exposed to an excess of driver. The driver D contains numerous DNA fragments in common with the tester T and therefore plays the role of competitive inhibitors by limiting self-hybridization of the DNA fragments of the tester common to the two populations.

The whole is subjected to a process of denaturation/renaturation during which three types of association will be produced according to the complementarity of the sequences.

The driver being in a large excess, the fragments common to both pools form mainly D/D hybrids (without adaptors) and also T/D hybrids (with an adaptor at the end of one of the two strands). Only the T/T hybrids possess at each end the adaptors which will be supplemented during the extension step preceding the PCR. By repeating the procedure several times after having selected the T/T duplexes, it is theoretically possible to purify the sequences present only in the tester. However, the efficiency of the subtrative hybridization technique is partly limited because of the great complexity of the human genome and of the abundance of genomic DNA sequences in any serum sample. The repetition of subtractive step results in a final enrichment factor of $10^2$ to $10^3$, whereas a factor of $10^6$ is sought.

It is therefore necessary to combine this method with a second so-called kinetics enrichment method. This is carried out by means of a PCR step which uses primers complementary to the adaptors added during the preceding step. The T/T duplexes are therefore exponentially amplified by PCR and the T/D duplexes undergo a linear amplification in which the derived fragments are single-stranded. The T/D hybrids are, for their part, not amplified. It is possible to destroy the single-stranded DNAs with a nuclease which spares the double-stranded DNAs. This method of selective enrichment of the double-stranded testers can be repeated with different adaptors in order to enrich the target DNA with respect to the other sequences of the tester after amplification. In general, three cycles of this reaction make it possible to obtain the enrichment factor of $10^6$ for the viral sequence to be sought. Subsequently, the products obtained are subcloned into a plasmid for sequencing and analysis.

I-2.2 Protocol

The RDA is carried out on the tester and driver samples using the DNAs from the patient previously mentioned.

Digestion of the Samples with the Restriction Enzyme RsaI

The procedure is carried out separately for the DNA of the tester and the DNA of the driver.

In order not to miss any lane, an RDA experiment was carried out in parallel with the RNAs on the same samples. However, no clones, whose sequence does not exhibit homology with known sequences, was able to be obtained from the viral RNA.

Preparation of the Following Mixture:

The mixture 10× RsaI buffer (5 µl), RsaI (10 U/µl) (1.5 µl), 43.5 µl nucleic acids (2 µg) is prepared. The mixture is incubated for 1 h 30 min at 37° C. and the reaction is stopped with 2.5 µl of 20× EDTA/glycogen. An extraction is carried out with 50 µl of phenol:chloroform:isoamyl alcohol (25:24:1). A centrifugation is carried out for 10 min at 14 000 rpm and the top aqueous phase is collected. Another extraction is carried out with 50 µl of chloroform:isoamyl alcohol (24:1), followed by a centrifugation for 10 min at 14 000 rpm and collection at the top aqueous phase. The aqueous phase is precipitated with 25 µl of 4M NH$_4$OAc and 187.5 µl of 95% ethanol, followed by centrifugation for 20 min at 14 000 rpm and removal of the supernatant. The pellet is washed with 200 µl of 80% ethanol. Another centrifugation is carried out for 5 min at 14 000 rpm and the supernatant is removed. The pellet is air-dried for 5 to 10 min and then dissolved in 5.5 µl of H$_2$O.

Ligation of the Tester to the Adaptors (which Contain the Sequences of the PCR Primers Necessary for the Final Phase of the Procedure):

1 µl of the tester is diluted in 5 µl of water. The ligation mixture is prepared as follows: H$_2$O (15 µl), 5× ligation buffer (BIOLABS) (10 µl), T4 DNA ligase (400 U/µl) BIOLABS (5 µl).

The mixture 1.1 was prepared as follows: tester 2 µl, adaptor 1 (10 µM) 2 µl, Master mix 6 µl.

The mixture 1.2 was prepared as follows: tester 2 µl, adaptor 2R (10 µM) 2 µl, Master mix 6 µl.

Preparation of the nonsubtracted control: 2 µl of the mixture 1.1 were added to 2 µl of the mixture 1.2. The mixture thus prepared is incubated overnight at 16° C. and the reaction is stopped by adding 1 µl of 20× EDTA/glycogen. The ligase is inactivated at 72° C. for 5 min and the mixture is cooled in ice.

Subtractive Hybridization: Tester—Driver.

The procedure is carried out separately for the DNA of the tester and the DNA of the driver.

First Hybridization:

Two mixtures H1 and H2 were prepared separately, consisting of the DNA of the tester ligated to the adaptor 1 (mixture H1) or the adaptor 2R (mixture H2). Mixture H1: driver 1.5 µl, "tester 1-1" 1.5 µl, 4× hybridization buffer 1 µl. Mixture H2: driver 1.5 µl, "tester 1-2" 1.5 µl, 4× hybridization buffer 1 µl. Oil was added to each of these mixtures and each mixture is incubated for 1 min 30 sec at 98° C. then for 6 h at 68° C. before immediately proceeding to the second hybridization.

Second Hybridization:

The following mixture is prepared: driver 1 µl, 4× hybridization buffer, 1 µl, H$_2$O 2 µl.

1 µl of the mixture is denatured at 98° C. for 1 min 30 sec.

15 µl of the mixture H2 are collected at the oil/sample interface. The air is aspirated, the driver is collected and the whole is added to the mixture H1. The whole is incubated at 68° C. overnight.

Dilution of the Subtracted DNAs:

To the hybridized tubes are added 200 µl of dilution buffer. The mixture, after aspirations and dischargings, is incubated at 68° C. for 7 min and the reaction is stopped in ice.

PCR on the RDA Products

The procedure is carried out separately on:
the RDA products derived from DNAs,
the nonsubtracted control, the subtracted control from the kit and the positive PCR control from the kit.

First Round of PCR:

The following mixture is prepared: H$_2$O 19.5 µl, 10× PCR buffer 2.5 µl, dNTPs (10 mM of each) 0.5 µl, PCR primer 1 (10 µM) 1 µl, 50× advantage cDNA polymerase mix 0.5 µl, RDA samples 1 µl.

The programme used is the following: 75° C. 5 min, 94° C. 30 sec

Then 25 cycles: 94° C. 10 sec, 66° C. 30 sec, 72° C. 1 min 30 sec

Second Round of PCR:

Use of 1 µl of first PCR product: the same mixture is used. 20 cycles are performed: 94° C. 10 sec, 68° C 30 sec, 72° C. 1 min 30 sec.

The pairs of primers of the Clontech PCR-select™ cDNA subtraction kit are used, they are located in the adaptors "linked" to the tester DNA at the beginning of the RDA procedure.

Analysis of 8 µl of sample on 1% agarose gel in 1× TBE with an ethidium bromide staining.

The RDA products are then ligated into the plasmid pTOPO using topoisomerase I, and then cloned into *E. coli* using the Invitrogen TOPO TA Cloning® Kit.

II. ANALYSIS OF THE RDA PRODUCTS

II-1. Screening of the Clones Generated by RDA

The RDA technique makes it possible to obtain, from tester and driver samples, PCR products which reflect what is potentially different between the two samples. This constitutes the material subtracted.

After cloning of the RDA products, 643 clones were screened according to the steps described below.

II-2. Replicas of the Products of Cloning

In order to remove a maximum of clones of human origin, the replicas of the "DNA" RDA clones are hybridized with probes corresponding to human genomic DNA digested with EcoRI/PstI and radiolabelled with $^{32}$P.

The results at the end of this screening are presented below.

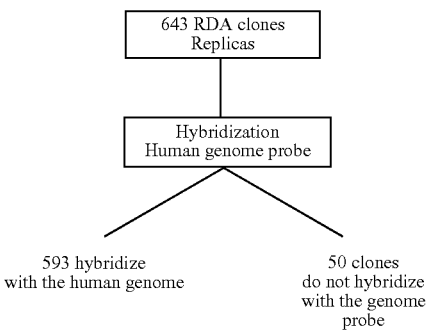

II-3. Interrogation of Data Banks

The fifty clones selected at the end of the first step are sequenced. Their respective sequences are compared to the known sequences in the data banks Swissprot, Embl, Genbank, Draft of the human genome. A number which are unknown appear. The results of the distribution of the sequences are given below.

| | |
|---|---|
| Phosphatase | 23% |
| Human DNA chromosomes 16 + 17 | 31% |
| Proteinase | 8% |
| Human immunoglobulin | 16% |
| Unknowns | 8% |

II-4. Additional Screening

Additional screening steps were carried out on the 4 clones selected in the preceding step according to the process described below.

Dot blot on the DNA of the clones selected using an EcoRI/PstI genomic DNA probe radiolabelled with $^{32}$P.

Southern blot of genomic DNA using, as probe, the clones previously selected, labelled with $^{32}$P.

At the end of these various steps, two "DNA" clones, whose sequences are unknown in the data banks, were selected.

The following step is the validation of the relevance of these data both to the samples obtained from patients suffering from hepatitis of undetermined aetiology and the controls consisting, on the one hand, of blood donors and, on the other hand, of patients suffering from pathologies of the liver of nonviral origin. For that, primers were synthesized within the DNA of the two clones and PCRs were performed using these primers on the genomic DNA extracted from the serum of blood donors in order to eliminate the possibility of the DNA of the clones corresponding to a DNA sequence which is frequent in the human genome.

One clone containing an insert of 1400 bp (XH) obtained from the RDA on the DNA was selected for its lack of homologies with the human genomic DNA and with any sequence present in the databases.

This sequence, rich in GC (62%) has several open reading frames. It is identified in SEQ ID NO: 1. The open reading frames are identified in SEQ ID NO: 2, 3, 4 and 5.

III. CHARACTERIZATION OF THE SEQUENCE ASSOCIATED WITH HEPATITIS X:XH

Four parallel approaches were used in order to characterize and specify the nature of the XH sequence isolated:
Bioclinical and epidemiological studies
"Molecular" approach
Production of specific antibodies
Electron microscopy study III-1. Bioclinical and Epidemiological Studies Different sets of primers and probes were synthesized in order to be able to amplify by PCR the XH sequence.

It is possible to use the following combination of primers:

```
Sense primer (1M13):
5'-CCCGCCCCGCTGATGAAAAG-3'      (SEQ ID NO: 10)

Anti-sense primer (3T7):
5'-ATGCCAACGCCCAGAGTCCG-3'      (SEQ ID NO: 13)
```

PCR cycles: 75° C. 5 min, 94° C. 2 min, 94° C. 10 s×28, 66° C. 30 s×28, 72° C. 1 min 30×28 and 72° C. 7 min.

Second round of PCR:

3 µl of samples from the 1$^{st}$ round were diluted with 27 µl of water.

The following mixture was prepared: H$_2$O 17.5 µl, 10× PCR buffer 2.5 µl, dNTPs (10 µM of each) 0.5 µl, nested PCR sense primer (10 µM) 1 µl, nested PCR anti-sense primer 2R (10 µM) 1 µl, 50× advantage cDNA polymerase mix 0.5 µl, RDA samples 1/10 2 µl.

The following pairs of primers were used:

```
Sense primer (1M13):
5'-CCCGCCCCGCTGATGAAAAG-3'      (SEQ ID NO: 10)

Anti-sense primer (1T7):
5'-GATGTTTCTGTGTCTGTGGG-3'      (SEQ ID NO: 14)
```

PCR cycles: 94° C. 2 min, 94° C. 10 s×10-15, 68° C. 30 s×10-15, 72° C. 1 min 30×10-15 and 72° C. 7 min.

First of all, 90 blood donors having normal transaminases were screened by PCR. All are negative for the XH sequence.

In parallel, the presence of the XH sequence at different dates in the serum of the patient having made it possible to carry out the RDA was sought. The presence of the XH sequence was observed only at the time when the transaminases were particularly high. Analysis of a liver biopsy from this patient after the fall in the transaminases reveals the presence of this sequence. It should be noted, in this case, that the patient has now been treated with interferon for 10 years and that any attempt to stop the treatment has as a consequence a rapid increase in the transaminases, suggesting the persistant presence of the agent implicated in the liver disease.

Twenty cases of primary biliary cirrhosis also remained negative for the XH sequence in the serum and the liver. Four cases of drug-induced hepatitis were also studied and also proved negative. Only 1/21 cases of autoimmune hepatitis and 1/7 cases of alcoholic hepatitis were positive for the XH sequence. These results on control populations made it possible to verify that the XH sequence is not usually present in "normal" human serum or in the context of liver lesions of nonviral aetiology.

Very advantageously, the analysis of liver and serum samples from patients of the Hôtel Dieu in Lyon, suffering from a chronic non-A, non-E hepatitis, made it possible to observe that 10% of them (11/109) are carriers of the XH sequence. A similar percentage of patients positive for the HXHV DNA is obtained in Moroccan patients having a chronic non-A, non-E hepatitis.

The patients positive by PCR in the serum for the XH sequence also appeared positive for the DNA extracted from liver biopsies when the biopsy was available. The presence of the XH sequence was able to be observed at different dates, several years apart, for the same patient.

Product amplified by PCR which were sequenced and show a very similar sequence from one patient to another.

These patients all have a chronic hepatitis with varying degrees at the level of the liver lesions, from minimal hepatitis to cirrhosis. Only some received blood transfusions, which constitutes a clearly established risk factor as for the transmission of the hepatitis virus. As these patients were not carriers of any known hepatitis virus, they were not subjected to any antiviral treatment protocol.

Furthermore, analysis of the thirteen cases of acute non-A, non-E hepatitis from Brazil allowed us to detect the presence of the XH sequence in eleven of these patients in the acute phase.

III-2. "Molecular" Approach

In order to determine the nature of the DNA isolated (single-stranded or double-stranded), the XH sequence was captured with alternately two oligonucleotides specific for either of the two DNA strands of the XH sequence attached to magnetic particles (Gene Trapper cDNA positive selection system, Gibco BRL (trade name)). The oligonucleotides used are the following:

```
sense oligonucleotide
S6M13:
5'-GCCATGTAACTCGGCAGTGC-3'      (SEQ ID NO: 9)

antisense oligonucleotide
Comp S6M13:
5'-GCACTGCCGAGTTACATGGC-3'      (SEQ ID NO: 15)
```

In a second instance, the products released after capture with the specific oligonucleotides are analysed by:
PCR and hybridization of the PCR products with a probe specific for XH.

Cloning, analysis of the clones by PCR, hybridizations of the replicas of the cloned products, sequencing of the clones.

This approach was validated on the XH sequence cloned into the TOPO vector. In this form, the sequence derived from the RDA is double-stranded since it is derived from a PCR. The capture procedure carried out on the cloned sequence finally makes it possible to capture the two DNA strands present.

The nature of the XH sequence which circulates in the patients was examined using several sera of "hepatitis X" patients, who were positive by PCR for the XH sequence. The sera are ultracentrifuged or not before the capture procedure.

All of these results demonstrate that only one of the oligonucleotides (the sense oligonucleotide, S6M13) is capable of retaining the XH sequence which circulates in the serum of the patients. Consequently, this sequence is at least partially single-stranded. This hypothesis on the single-stranded nature of the XH DNA is supported by trials of preliminary treatments of the XH DNA with S1 nuclease, an enzyme which is specific for the single-stranded forms of DNA. Preliminary treatment of extracts of sera positive for XH DNA abolishes the PCR signal and therefore confirms the single-stranded nature of the sequence.

III-3. Production of Specific Antibodies

The XH sequence (SEQ ID NO: 1) has four open reading frames. ORF1 is presented in SEQ ID NO: 2, it comprises 101 amino acids encoded by bases 1 to 103 of SEQ ID NO: 1. ORF2 is presented in SEQ ID NO: 3, it comprises 135 amino acids encoded by bases 829 to 1233 of SEQ ID NO: 1. ORF3 is presented in SEQ ID NO: 4, it comprises 135 amino acids encoded by bases 270 to 674 of SEQ ID NO: 1. ORF4 is presented in SEQ ID NO: 5, it comprises 183 amino acids encoded by bases 813 to 1361 of SEQ ID NO: 1. By computer analysis, it was shown that the protein selected possesses a region of 14 amino acids which has all the immunogenicity and hydrophilicity properties required to induce the production of antibodies.

A polypeptide corresponding to the abovementioned region of 14 amino acids was synthesized for the production of polyclonal antibodies. The sequence of this polypeptide is given below and identified by a reference in SEQ ID NO: 6.

RRAAELHRRDQYRL

For the immunization of the rabbits, a cysteine (C) was added to the COOH-terminal end of this polypeptide for coupling to BSA. The immunogen RRAAELHRRDQYRLC-BSA was injected into rabbits in an amount of 100 µg of immunogen per rabbit and per injection. The immunization protocol used is the following:

D0: 1st taking of 10 ml of blood, immunization: 0.1 mg of immunogen (1 mg/ml)+0.4 ml of physiological saline+0.5 ml CFA 1 ml ID (0.1 ml×10)

D28: 0.1 mg of immunogen (1 mg/ml)+0.4 ml of physiological saline+0.5 ml IFA ID-1 ml ID (0.1 ml×10)

D56: 0.1 mg of immunogen (1 mg/ml)+0.4 ml of physiological saline+0.5 ml IFA-1 ml SC (0.25 ml×4)

D63: 1st taking of 3 ml of blood from the ear without anticoagulant

D84: 0.1 mg of immunogen (1 mg/ml)+0.4 ml of physiological saline+0.5 ml AFI 1 ml IM (0.25 ml×4)

D91: 2nd taking of 9 ml of blood from the ear without anticoagulant

D112: 0.1 mg of immunogen (1 mg/ml)+0.4 ml of physiological saline+0.5 ml IFA-1 ml ID (0.1 ml×10)

D119: 3rd taking of 9 ml of blood from the ear without anticoagulant.

The production of specific antibodies is a very effective tool for screening for the expression of the XH sequence on biopsies from non-A, non-E patients in parallel with other categories of patients or controls.

The polypeptide of 14 amino acids (SEQ ID NO: 6) is used to develop an ELISA test for the capture of antibodies specific for the HXHV virus potentially present in patients having a chronic non-A, non-E hepatitis. Into the wells of a microtitre plate are deposited 100 µl of streptavidin diluted 1/100 in carbonate buffer. The deposition is followed by incubation for 2 hours at 37° C. in an incubator, after which three washes are carried out. 100 µl of biotinylated peptide, diluted 1/100 in PBS, are then added to each of the wells. The mixture is incubated overnight at 40° C. Three washes are then carried out. 250 µl of PBS+goat serum are then added in order to saturate the sites. The whole is incubated for 2 hours at 37° C. After three washes, 100 µl of each serum to be tested (diluted at the appropriate dilution in PBS Tween+SC) are added and an incubation is carried out for 2 hours at 37° C. in an incubator. Three washes are then carried out and 100 µl of a dilute solution of anti-human IgG antibody coupled to peroxidase are deposited. The whole is incubated in an incubator for one hour at 37° C. Incubation is followed by a step of three washes. The visualization is carried out by adding ortho-phenylenediamine (100 µl). The reaction is blocked by adding 50 µl of $H_2SO_4$ and the reading is carried out at OD 492 nm and 635 nm. The results are presented in the appended figure. As is evident from this figure, 6 patients are very well detected by this technique among the 16 in whom the XH sequence had been detected by PCR. The seventh patient is weakly detected, at the limit of the threshold.

III-4. Electron Microscopy Study

Sucrose gradients were prepared in order to isolate possible viral particles associated with the presence of the XH sequence. For that, the serum of a patient of the non-A, non-E hepatitis cohort was used. Two consecutive fractions of this gradient appeared positive by PCR for the XH sequence. These fractions correspond to densities of the order of 1.2 to 1.5 g/cm$^3$. The electron microscopy study made it possible to observe particles whose size and regularity (110 nm diameter) are compatible with that of a viral agent. The frequency with which these particles are observed in electron microscopy suggests a concentration of the order of $5 \times 10^5$ particles/ml of serum. The ELISA test developed allowed us to search for the presence of "anti-XH" antibodies in blood donors and in various categories of patients.

IV. STUDY OF BLOOD DONORS AND PATIENTS

IV-1. Search for Anti-XH Antibodies

The search for anti-XH antibodies in blood donors and in various categories of patients was carried out by the ELISA test. The results are presented in the table below.

TABLE

|  | Blood donors | | Patients | | | | | | |
| --- | --- | --- | --- | --- | --- | --- | --- | --- | --- |
|  | TN | TE | VHC+ | VHB+ | HIV+ | Non-A–E* | Non-A–E** | H* | H** |
| Total number studied | 408 | 389 | 45 | 40 | 31 | 44 | 13 | 47 | 41 |
| % of anti-XH positives | 1.22 | 6.2 | 3 | 16 | 35 | 23 | 31 | 36 | 17 |

TN means "blood donors having a normal transaminase level"
TE means "blood donors having a high transaminase level"
HCV+ means "HCV-positive patients"
HBV+ means "HBV-positive patients"
HIV+ means "HIV-positive patients"
Non A–E* means "patients suffering from a chronic non-A–E hepatitis"
Non A–E** means "patients suffering from a fulminant non-A–E hepatitis"
H* means "haemophilic patients who received blood transfusions before 1987, that is to say before treating blood with detergent solvents"
H** means "haemophilic patients who received blood transfusions after 1987"

The difference in prevalence of the anti-XH antibodies between the 408 blood donors having normal transaminases and the 389 blood donors having high transaminases is significant. This difference, observed between these two groups tested according to a double blind design, suggests a causal relationship between the presence of the anti-XH antibodies and the hepatic disease. A fraction of the blood donors having high transaminases (20%) is found to be positive by PCR for the XH sequence. This sequence was never found in the blood donors having normal transaminases.

A higher percentage of positivity in anti-XH antibodies is found for the HIV-positive patients (35%), compared to the 16% in the patients who are chronic carriers of HBV and to the 3% in the chronic carriers of HCV. Detailed study of the risk factors to which the patients were exposed demonstrates that the XH sequence is transmissible by the parenteral and sexual route.

Only the patients having a chronic or fulminant non-A, non-E hepatitis positive in ELISA are positive by PCR in 50% of the cases, whereas no positive for DNA was detected in the HCV or HBV group of patients or among the haemophiliacs.

A study was also carried out on patients suffering from acute hepatitis of unknown aetiology progressing to chronicity or cure. Of 13 cases studied, 11 proved positive for anti-XH antibodies during the acute phase of the disease. Among the cases which were able to be monitored, all remained positive for antibodies during this time.

IV-2. Search for the XH Sequence by PCR

A real-time quantitative PCR method using the Roche® Light cycler was developed in order to amplify the XH sequence. It was used, inter alia, to amplify the XH sequence in the ORF 4 in the 11 patients who were found to be positive for anti-XH antibodies.

The four specific primers described below were synthesized and purified by HPLC.

```
S1 (sense):
5'-GCGTTGTGGTTCTGTTGC-3'      (SEQ ID NO: 19)

S2 (sense):
5'-GATCAATATCGCCTACGC-3'      (SEQ ID NO: 20)

AS1 (anti-sense):
5'-CTGAAGGATAGGGCTGATG-3'     (SEQ ID NO: 21)

AS2 (anti-sense):
5'-CTGTTCGCCAGCCACCAG-3'      (SEQ ID NO: 22)
```

The PCR is carried out using a Qiagen® kit "QuantiTect SYBR Green PCR Kit" (trade name).

The composition of the reaction mixture is the following

| | |
| --- | --- |
| Master mix quantitect Qiagen | 10 µl |
| Sense primer (15 µM) | 1 µl |
| Anti-sense primer (15 µM) | 1 µl |
| Target DNA | 5 µl |
| Water (without RNAse) | 3 µl |
| Total volume per capillary tube | 20 µl |

Once the 20 µl have been depositied, the capillary tubes are sealed, briefly centrifuged and placed in the rotor of the Light Cycler.

PCR Protocol

Activation:
95° C. for 15 minutes.
Amplification/quantification:
Number of cycles 45

| | Denaturation | Annealing | Extension |
| --- | --- | --- | --- |
| Temperature [° C.] | 95 | 52 | 72 |
| Incubation [s] | 0 | 5 | Tx* |
| Level of temperature transition [° C./s] | 20 | 20 | 20 |

Tx*: temperature depending on the combination of primers used.

| Primers | Size of the amplicon (bp) | Tx (s) |
| --- | --- | --- |
| S1/AS1 | 441 | 18 |
| S1/AS2 | 312 | 13 |
| S1/AS2 | 331 | 13 |
| S2/AS2 | 232 | 10 |

Analysis of the Melting Curve:

|  | Denaturation | Annealing | Extension |
|---|---|---|---|
| Temperature [° C.] | 95 | 40 | 95 |
| Incubation [s] | 0 | 5 | 0 |
| Level of temperature transition [° C./s] | 20 | 20 | 0.3 |

Cooling:

40° C. for 30 seconds.

Characterization of the Threshold for Detection of the Sequence of Interest

The theoretical detection threshold for the XH sequence inserted into the plasmid is between 1 and 2 copies per capillary tube. The Tm of the amplicon S1/AS2 (312 bp) most frequently used is 88° C.

The application of this technique shows, inter alia, that four out of five of the patients who progressed to a chronic hepatitis are positive by PCR for the XH sequence. Conversely, five out of six of the patients who were cured became negative by PCR for the XH sequence.

The invention claimed is:

1. An isolated DNA nucleotide fragment, comprising a nucleotide sequence of at least 40 contiguous nucleotides belonging to the segment starting at nucleotide 813 and ending at nucleotide 1361 of the sequence set forth in SEQ ID NO: 1, or the complementary sequence of said segment.

2. An isolated DNA nucleotide fragment, comprising a nucleotide sequence of at least 40 contiguous nucleotides belonging to the segment starting at nucleotide 927 and ending at nucleotide 968 of the sequence set forth in SEQ ID NO: 1, or the complementary sequence of said segment.

3. An isolated DNA nucleotide fragment, comprising the sequence set forth in SEQ ID NO: 1 or its full-length complementary sequence.

4. An expression cassette, which is functional in a cell derived from a prokaryotic or eukaryotic organism, allowing the expression of a nucleic acid sequence according to claim 1, placed under the control of elements necessary for its expression.

5. A vector comprising an expression cassette according to claim 4.

6. An isolated cell derived from a eukaryotic or prokaryotic organism comprising an expression cassette according to claim 4.

7. Cell according to claim 6, derived from a eukaryotic organism chosen from COS cells or CHO cells.

8. Cell according to claim 6, derived from a lower eukaryotic organism chosen from *Saccharomyces cerevisiae* cells or *Pichia pastoris* cells.

9. A method for preparing a polypeptide, comprising culturing a host cell as defined in claim 6 in an appropriate culture medium, obtaining said polypeptide and purifying said polypeptide to the required degree of purity.

10. A primer or probe capable of hybridizing with a nucleic acid sequence as defined in claim 1, wherein the primer or probe is chosen from any one of the sequences SEQ ID NOS: 19-22.

11. A diagnostic composition, comprising at least one probe or one primer as defined in claim 10.

12. A method of detecting HXHV DNA or RNA in a biological sample, comprising:
 (i) Contacting a sample suspected of containing HXHV nucleic acid with at least one probe or primer comprising 12 or more contiguous nucleotides of the segment of nucleotides 813-1361 of SEQ ID NO: 1 or the complement thereof, and then
 (ii) demonstrating hybridization of said probe or primer to said HXHV DNA or RNA or amplification of said HXHV DNA or RNA,
 wherein demonstration of said hybridization or amplification indicates the presence of HXHV DNA or RNA.

13. A vector comprising a nucleotide sequence encoding:
(i) Either at least one polypeptide or polypeptide fragment encoded by a DNA nucleotide fragment according to claim 1, or
(ii) an antibody or a binding fragment thereof capable of binding to at least one polypeptide of polypeptide fragment as defined in (i).

14. An immunogenic composition comprising a vector as defined in claim 13, wherein said nucleotide sequence is placed under the control of elements ensuring its expression in vivo.

15. An isolated genetically modified eukaryotic cell transformed with a DNA nucleotide fragment according to claim 1.

16. An immunogenic composition comprising a cell as defined in claim 15.

17. A transformed cell of claim 15 which is derived from one of the following types:
COS or CHO cell-lines or *Saccharomyces cerevisiae* or *Pichia pastoris* cells.

18. The immunogenic composition of claim 16, wherein the cell is derived from one of the following types: COS or CHO cell-lines or *Saccharomyces cerevisiae* or *Pichia pastoris* cells.

* * * * *

SEQUENCE LISTING

```
<160> NUMBER OF SEQ ID NOS: 22

<210> SEQ ID NO 1
<211> LENGTH: 1362
<212> TYPE: DNA
<213> ORGANISM: HXHV virus

<400> SEQUENCE: 1
actaccaaca gatcctcgac gaactgcgcc aggaactggc cgagcactac ctgctgcgca      60
gcgacctggc gatccaggat atcgcctgct acctcggttt caccgagtca cgctcgttcc     120
accgcagttt caagagctgg accgggcaga cgccgggcga gtttcgcgag agccggcgcc     180
gggataatcc gctgggctag cgcgatatgg ccggaaacgc cgtgccagcc agtagtcgag     240
actcaaccat cgccccgccc cgctgatgaa aagcgccacg agcgcagcca cggccggcac     300
cggtgaggtt tgccaatggc atatcagtcc tcccggcgcc cttactcgtt cttatcgcca     360
ctgcacgtgc cttcaatacg ggagccttcc tgcgccttct cggcagcggt caggctgtag     420
ccgccggcca gttcctgctc agcgaagggg atgctagtgg cgtgggcagt gaacgccatg     480
taactcggca gtgcagcgcc ctagggtctg ttgccgtttc gcgcacggcc gcgtcgaaac     540
ggcaacagac cctaggtggc agtcagggta ttggcatctc tccatcggtt tcgaatacgg     600
cgccaggttg gcgccctcgc agcaatggac gaggcaggga tgcgggcgtt acagcgggcg     660
aaaaagattt ctcgtagccc gatgaaatac gggggcgctt tgctcgccag caatcgcggc     720
tacgactgca tggacgcagg aggtagagcg aagcaggatg vvagagcaga aagctctctc     780
ccacagacac agaaacatcc accgcacggt aggaggtgat tcaaatgatc aggcatctcc     840
tctggttgga ctgcatggcc gctgcgagca cgggcgttgt ggttctgttg ctggccccc      900 tggttgagcg gctggtatgc cctgcccggc gagctgctga gcttcatcgg cgcgatcaat     960
atcgcctacg cctgcttttc catttcgctg gcgattcgcc tgcgacgcgc cgaagcgcta    1020
atcaagctgc tggcagtggc caacggactc tgggcgttgg catgccttgg catcgctacg    1080
atctttgccc cgctcatgac gctaccgggg ctttgtcatg tgctcggcga ggctgcatcc    1140
gtcgcaggcc tgggcatgct ggagtggaaa tggcgcaggc agctgctggt ggctggcgaa    1200
cagggcgttt cgactcagct tgtcgcggtc cagtaaccgt cacaggtatt caggcgaaga    1260
tccggcgatg gctgttcagg ccatcatcag ccctatcctt cagccctgtg aaagcggttc    1320
ttgcccgcgt gcttggccgc gtacctcggc cccgaccacg ct                      1362

<210> SEQ ID NO 2
```

-continued

<211> LENGTH: 101
<212> TYPE: PRT
<213> ORGANISM: HXHV virus

<400> SEQUENCE: 2

Thr Thr Asn Arg Ser Ser Thr Asn Cys Ala Arg Asn Trp Pro Ser Thr
1 5 10 15

Thr Cys Cys Ala Ala Thr Trp Arg Ser Arg Ile Ser Pro Ala Thr Ser
20 25 30

Val Ser Pro Ser His Ala Arg Ser Thr Ala Val Ser Arg Ala Gly Pro
35 40 45

Gly Arg Arg Arg Ala Ser Phe Ala Arg Ala Gly Ala Gly Ile Ile Arg
50 55 60

Trp Ala Ser Ala Ile Trp Pro Glu Thr Pro Cys Gln Pro Val Val Glu
65 70 75 80

Thr Gln Pro Ser Pro Arg Pro Ala Asp Glu Lys Arg His Glu Arg Ser
85 90 95

His Gly Arg His Arg
100

<210> SEQ ID NO 3
<211> LENGTH: 135
<212> TYPE: PRT
<213> ORGANISM: HXHV virus

<400> SEQUENCE: 3

Ser Gly Ile Ser Ser Gly Trp Thr Ala Trp Pro Leu Arg Ala Arg Ala
1 5 10 15

Leu Trp Phe Cys Cys Trp Pro Pro Trp Leu Ser Gly Trp Tyr Ala Leu
20 25 30

Pro Gly Glu Leu Leu Ser Phe Ile Gly Ala Ile Asn Ile Ala Tyr Ala
35 40 45

Cys Phe Ser Ile Ser Leu Ala Ile Arg Leu Arg Arg Ala Glu Ala Leu
50 55 60

Ile Lys Leu Leu Ala Val Ala Asn Gly Leu Trp Ala Leu Ala Cys Leu
65 70 75 80

Gly Ile Ala Thr Ile Phe Ala Pro Leu Met Thr Leu Pro Gly Leu Cys
85 90 95

His Val Leu Gly Glu Ala Ala Ser Val Ala Gly Leu Gly Met Leu Glu
100 105 110

Trp Lys Trp Arg Arg Gln Leu Leu Val Ala Gly Glu Gln Gly Val Ser
115 120 125

Thr Gln Leu Val Ala Val Gln
130 135

<210> SEQ ID NO 4
<211> LENGTH: 135
<212> TYPE: PRT
<213> ORGANISM: HXHV virus

<400> SEQUENCE: 4

Lys Ala Pro Arg Ala Gln Pro Arg Pro Ala Pro Val Arg Phe Ala Asn
1 5 10 15

Gly Ile Ser Val Leu Pro Ala Pro Leu Leu Val Leu Ile Ala Thr Ala
20 25 30

Arg Ala Phe Asn Thr Gly Ala Phe Leu Arg Leu Leu Gly Ser Gly Gln
35 40 45

-continued

```
Ala Val Ala Ala Gly Gln Phe Leu Leu Ser Glu Gly Asp Ala Ser Gly
     50                  55                  60

Val Gly Ser Glu Arg His Val Thr Arg Gln Cys Ser Ala Leu Gly Ser
 65                  70                  75                  80

Val Ala Val Ser Arg Thr Ala Ala Ser Lys Arg Gln Gln Thr Leu Gly
                 85                  90                  95

Gly Ser Gln Gly Ile Gly Ile Ser Pro Ser Val Ser Asn Thr Ala Pro
            100                 105                 110

Gly Trp Arg Pro Arg Ser Asn Gly Arg Gly Arg Asp Ala Gly Val Thr
        115                 120                 125

Ala Gly Glu Lys Asp Phe Ser
    130                 135

<210> SEQ ID NO 5
<211> LENGTH: 183
<212> TYPE: PRT
<213> ORGANISM: HXHV virus

<400> SEQUENCE: 5

Glu Val Ile Gln Met Ile Arg His Leu Leu Trp Leu Asp Cys Met Ala
  1               5                  10                  15

Ala Ala Ser Thr Gly Val Val Val Leu Leu Leu Ala Pro Leu Val Glu
             20                  25                  30

Arg Leu Val Cys Pro Ala Arg Arg Ala Ala Glu Leu His Arg Arg Asp
         35                  40                  45

Gln Tyr Arg Leu Arg Leu Leu Phe His Phe Ala Gly Asp Ser Pro Ala
     50                  55                  60

Thr Arg Arg Ser Ala Asn Gln Ala Ala Gly Ser Gly Gln Arg Thr Leu
 65                  70                  75                  80

Gly Val Gly Met Pro Trp His Arg Tyr Asp Leu Cys Pro Ala His Asp
                 85                  90                  95

Ala Thr Gly Ala Leu Ser Cys Ala Arg Arg Gly Cys Ile Arg Arg Arg
            100                 105                 110

Pro Gly His Ala Gly Val Glu Met Ala Gln Ala Ala Ala Gly Gly Trp
        115                 120                 125

Arg Thr Gly Arg Phe Asp Ser Ala Cys Arg Gly Pro Val Thr Val Thr
    130                 135                 140

Gly Ile Gln Ala Lys Ile Arg Arg Trp Leu Phe Arg Pro Ser Ser Ala
145                 150                 155                 160

Leu Ser Phe Ser Pro Val Lys Ala Val Leu Ala Arg Val Leu Gly Arg
                165                 170                 175

Val Pro Arg Pro Arg Pro Arg
            180

<210> SEQ ID NO 6
<211> LENGTH: 14
<212> TYPE: PRT
<213> ORGANISM: HXHV virus

<400> SEQUENCE: 6

Arg Arg Ala Ala Glu Leu His Arg Arg Asp Gln Tyr Arg Leu
  1               5                  10

<210> SEQ ID NO 7
<211> LENGTH: 16
<212> TYPE: DNA
<213> ORGANISM: Artificial sequence
<220> FEATURE:
```

```
<223> OTHER INFORMATION: Description of the artificial sequence: primer
      6B1

<400> SEQUENCE: 7
taccaacaga tcctcg                                                          16

<210> SEQ ID NO 8
<211> LENGTH: 16
<212> TYPE: DNA
<213> ORGANISM: Artificial sequence
<220> FEATURE:
<223> OTHER INFORMATION: Description of the artificial sequence: primer
      6B.A

<400> SEQUENCE: 8
atatcgcctg ctacct                                                          16

<210> SEQ ID NO 9
<211> LENGTH: 20
<212> TYPE: DNA
<213> ORGANISM: Artificial sequence
<220> FEATURE:
<223> OTHER INFORMATION: Description of the artificial sequence: primer
      S6M13

<400> SEQUENCE: 9
gccatgtaac tcggcagtgc                                                      20

<210> SEQ ID NO 10
<211> LENGTH: 20
<212> TYPE: DNA
<213> ORGANISM: Artificial sequence
<220> FEATURE:
<223> OTHER INFORMATION: Description of the artificial sequence: primer
      1M13

<400> SEQUENCE: 10
cccgccccgc tgatgaaaag                                                      20

<210> SEQ ID NO 11
<211> LENGTH: 15
<212> TYPE: DNA
<213> ORGANISM: Artificial sequence
<220> FEATURE:
<223> OTHER INFORMATION: Description of the artificial sequence: primer
      6B antisens

<400> SEQUENCE: 11
tatgccattg gcaaa                                                           15

<210> SEQ ID NO 12
<211> LENGTH: 18
<212> TYPE: DNA
<213> ORGANISM: Artificial sequence
<220> FEATURE:
<223> OTHER INFORMATION: Description of the artificial sequence: primer
      6B.B

<400> SEQUENCE: 12
atggttgagt ctcgacta                                                        18

<210> SEQ ID NO 13
<211> LENGTH: 20
<212> TYPE: DNA
<213> ORGANISM: Artificial sequence
<220> FEATURE:
<223> OTHER INFORMATION: Description of the artificial sequence: primer
```

```
                                  3T7

<400> SEQUENCE: 13
atgccaacgc ccagagtccg                                               20

<210> SEQ ID NO 14
<211> LENGTH: 20
<212> TYPE: DNA
<213> ORGANISM: Artificial sequence
<220> FEATURE:
<223> OTHER INFORMATION: Description of the artificial sequence: primer
      1T7

<400> SEQUENCE: 14
gatgtttctg tgtctgtggg                                               20

<210> SEQ ID NO 15
<211> LENGTH: 20
<212> TYPE: DNA
<213> ORGANISM: Artificial sequence
<220> FEATURE:
<223> OTHER INFORMATION: Description of the artificial sequence: primer
      Comp S6M13

<400> SEQUENCE: 15
gcactgccga gttacatggc                                               20

<210> SEQ ID NO 16
<211> LENGTH: 36
<212> TYPE: DNA
<213> ORGANISM: Artificial sequence
<220> FEATURE:
<223> OTHER INFORMATION: Description of the artificial sequence: probe
      6B

<400> SEQUENCE: 16
tccgctgggc tagcgcgata tggccggaaa cgccgt                             36

<210> SEQ ID NO 17
<211> LENGTH: 40
<212> TYPE: DNA
<213> ORGANISM: Artificial sequence
<220> FEATURE:
<223> OTHER INFORMATION: Description of the artificial sequence: probe
      PAS

<400> SEQUENCE: 17
atggacgagg cagggatgcg ggcgttacag cgggcgaaaa                         40

<210> SEQ ID NO 18
<211> LENGTH: 30
<212> TYPE: DNA
<213> ORGANISM: Artificial sequence
<220> FEATURE:
<223> OTHER INFORMATION: Description of the artificial sequence: probe
      T7

<400> SEQUENCE: 18
ccttcctgcg ccttctcggc agcggtcagg                                    30

<210> SEQ ID NO 19
<211> LENGTH: 18
<212> TYPE: DNA
<213> ORGANISM: Artificial sequence
<220> FEATURE:
<223> OTHER INFORMATION: Description of the artificial sequence: primer
      S1
```

-continued

```
<400> SEQUENCE: 19 gcgttgtggttctgttgc                                                        18

<210> SEQ ID NO 20
<211> LENGTH: 18
<212> TYPE: DNA
<213> ORGANISM: Artificial sequence
<220> FEATURE:
<223> OTHER INFORMATION: Description of the artificial sequence: primer
      S2

<400> SEQUENCE: 20 gatcaatatcgcctacgc                                                        18

<210> SEQ ID NO 21
<211> LENGTH: 19
<212> TYPE: DNA
<213> ORGANISM: Artificial sequence
<220> FEATURE:
<223> OTHER INFORMATION: Description of the artificial sequence: primer
      AS1

<400> SEQUENCE: 21 ctgaaggatagggctgatg                                                       19

<210> SEQ ID NO 22
<211> LENGTH: 18
<212> TYPE: DNA
<213> ORGANISM: Artificial sequence
<220> FEATURE:
<223> OTHER INFORMATION: Description of the artificial sequence: primer
      AS2

<400> SEQUENCE: 22 ctgttcgccagccaccag                                                        18
```